(12) United States Patent
Datta

(10) Patent No.: US 7,628,788 B2
(45) Date of Patent: Dec. 8, 2009

(54) ABLATION CATHETER WITH IMPROVED TIP COOLING

(75) Inventor: Keshava Datta, Chino Hills, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 415 days.

(21) Appl. No.: 11/322,583

(22) Filed: Dec. 30, 2005

(65) Prior Publication Data

US 2007/0156131 A1  Jul. 5, 2007

(51) Int. Cl.
*A61B 18/14* (2006.01)
(52) U.S. Cl. ........................................ 606/41
(58) Field of Classification Search ............ 604/20, 604/35; 606/32, 39–41, 45, 49
See application file for complete search history.

(56) References Cited

U.S. PATENT DOCUMENTS

| 6,413,256 | B1 * | 7/2002 | Truckai et al. ............... 606/41 |
| 2002/0198520 | A1 * | 12/2002 | Coen et al. ................... 606/41 |
| 2003/0004506 | A1 * | 1/2003 | Messing ..................... 606/41 |
| 2004/0204707 | A1 * | 10/2004 | Hood et al. ................... 606/41 |
| 2004/0231683 | A1 | 11/2004 | Eng et al. |

FOREIGN PATENT DOCUMENTS

DE  10030111 A1  1/2002

| WO | WO 01/21069 A | 3/2001 |
| WO | WO 2005/112814 A2 | 1/2005 |

OTHER PUBLICATIONS

European Search Report dated Oct. 4, 2007, for European Application No. 06256631.0, in the name of Biosense Webster, Inc.
European Search Report dated May 21, 2007, for European Application No. 06256632.8, in the name of Biosense Webster, Inc.

* cited by examiner

*Primary Examiner*—Lee S Cohen
*Assistant Examiner*—Vincent Sica
(74) *Attorney, Agent, or Firm*—Christie, Parker & Hale, LLP.

(57) ABSTRACT

A catheter has a catheter body having an outer wall, proximal and distal ends, and at least one lumen extending therethrough. A tip section distal the catheter body includes an irrigated tip electrode and a segment of flexible tubing with at least one lumen therethrough. The tip electrode has a stepped profile which provides laminar flow (or at least minimizes turbulent flow and eddies) of irrigation/cooling fluid over its surface, which in turn provides more uniform cooling of the tip electrode, particularly where the tip electrode is elongated. In one embodiment, the tip electrode has a longitudinal axis, an outer ring surface generally perpendicular to the longitudinal axis, and an outer cylindrical surface extending distally from the outer ring surface along the longitudinal axis. Openings are provided in the outer ring surface to permit fluid (e.g., saline) to pass from an interior of the tip electrode to the outer ring surface and flow in a laminar manner over the cylindrical surface.

9 Claims, 8 Drawing Sheets

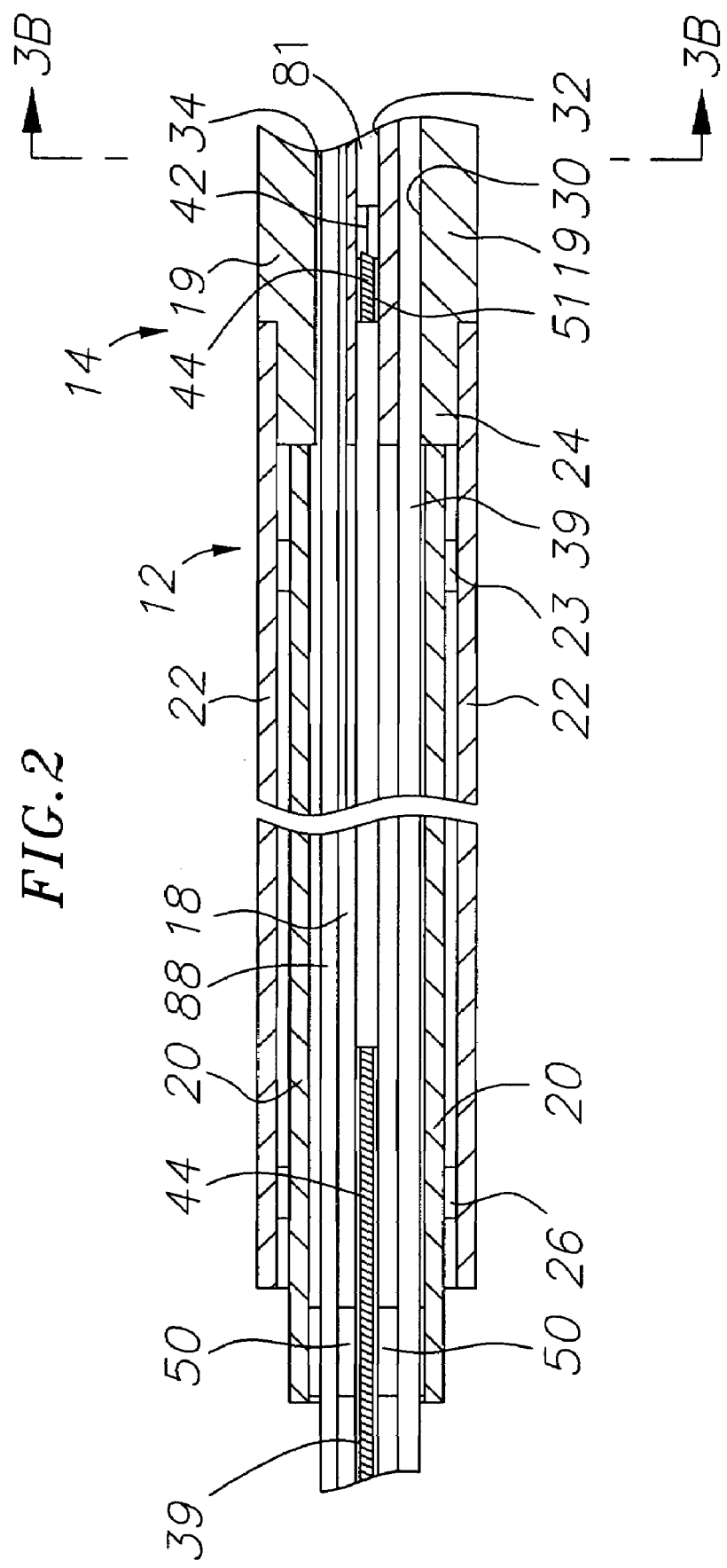

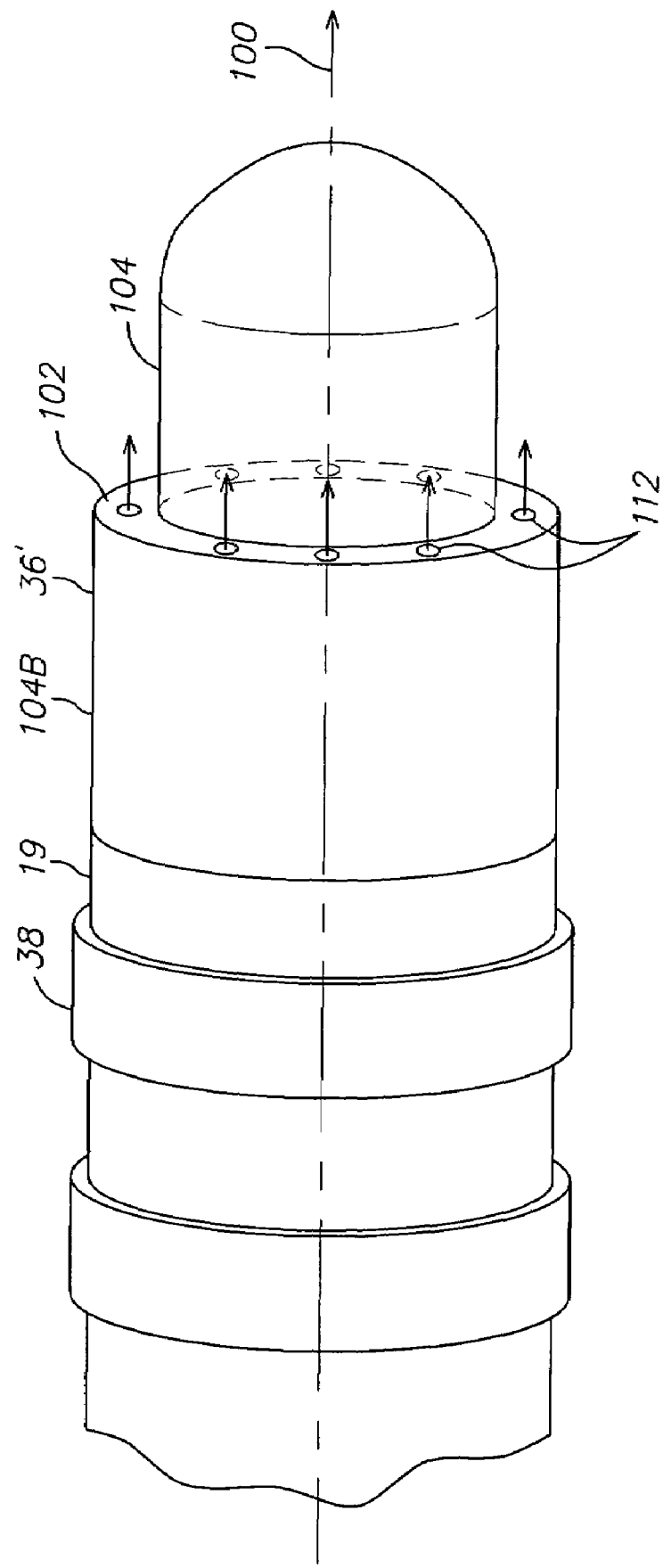

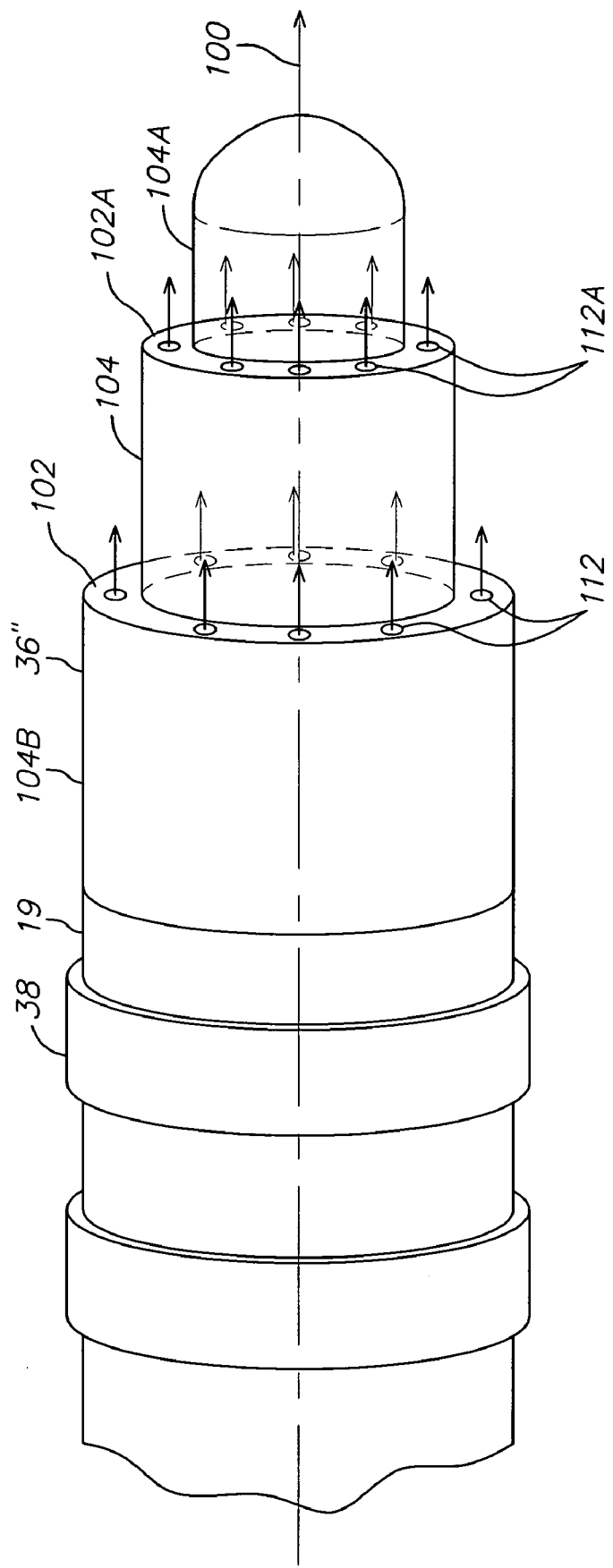

ABLATION CATHETER WITH IMPROVED TIP COOLING

FIELD OF THE INVENTION

The present invention relates to ablation catheters, and in particular to irrigated ablation catheters with improved cooling of the tip electrode.

BACKGROUND OF THE INVENTION

The heart has a natural pacemaker and conduction system which causes the heart muscle to contract, or beat, in an orderly rhythmical manner. The normal pacing rate for an adult at rest is about 60 to 70 beats per minute. There are many physiologic abnormalities which cause one or more chambers of the heart to beat more rapidly (tachycardia or flutter) or chaotically (fibrillation). A patient cannot live with ventricular fibrillation because there would be no blood pumped through the arteries, but may live with atrial fibrillation so long as the chaotic impulses are filtered out at the AV node and do not reach the ventricles. A patient may also live with atrial flutter and various forms of tachycardia but quality of life may be considerably compromised.

Many of these arrhythmias can be treated effectively by ablation (burning) using radio-frequency (RF) energy. Other arrhythmias are less effectively treated, requiring more RF lesions for a successful outcome or resulting in no successful outcome. RF ablation is performed with a catheter having one or more electrodes which deliver the RF energy to the cardiac tissue. In an operation the catheter is guided through a vein or artery into the heart chamber and positioned at one or more sites, determined by an electrophysiologist, to correct the arrhythmia. The catheter delivers energy from an external source (generator) to the tissue, generating sufficient heat to kill the tissue, which is thereafter replaced by scar tissue. In a successful ablation procedure, the lesions formed interrupt the electrical pathways that cause the arrhythmia so that heart rhythm is improved or returns to normal.

Atrial fibrillation is a common sustained cardiac arrhythmia and a major cause of stroke. This condition is perpetuated by reentrant wavelets propagating in an abnormal atrial-tissue substrate. It is believed that to treat atrial fibrillation by radio-frequency ablation using a catheter, continuous linear lesions must be formed to segment the heart tissue. By segmenting the heart tissue, no electrical activity can be transmitted from one segment to another. Preferably, the segments are made small when segmenting the fibrillatory tissue.

A preferred technique for treating atrial fibrillation by radio-frequency ablation is where a relatively long electrode can be held stationary in good contact with the heart wall while ablation is completed. In this way, a continuous transmural burn may be effected. In use, the electrode catheter is inserted into a major vein or artery, e.g., femoral, artery, and then guided into the chamber of the heart which is of concern. Within the heart, the ability to control the exact position and orientation of the catheter tip is critical and largely determines how useful the catheter is. In certain applications, it is desirable to have the ability to inject and/or withdraw fluid through the catheter. This is accomplished by means of an irrigated tip catheter.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause a lesion. Heating of the electrode results from conduction from the heated tissue. While the blood circulating around the ablation electrode tends to cool it, a stagnant area between the electrode and the tissue may be heated to such a temperature that a thin, transparent coating of blood protein forms on the surface of the tip electrode. This causes an impedance rise. When this occurs, the catheter must be removed and the tip electrode cleaned.

When RF current is applied to an ablation electrode in good contact with the endocardium to create a lesion, the temperature of the endocardium drops off very rapidly with distance from the electrode. The resulting lesion tends to be hemispherical, usually about 6 mm in diameter and about 3 to 4 mm deep. When a tip electrode is irrigated, e.g., with room temperature saline, the tip electrode is cooled by the flow of saline through it and the surface of the electrode is flushed. Because the strength of the RF current is no longer limited by the interface temperature, current can be increased. This results in lesions which tend to be larger and more spherical. It can be seen, then, that there is a need for an ablation catheter with an efficient method of cooling the tip electrode thereby allowing for better penetration due to lower interface temperatures.

SUMMARY OF THE INVENTION

A catheter in accordance with the present invention includes a catheter body having an outer wall, proximal and distal ends, and at least one lumen extending therethrough. A tip section distal the catheter body includes an irrigated tip electrode and a segment of flexible tubing with at least one lumen therethrough. The tip electrode has a stepped profile which provides laminar flow (or at least minimizes turbulent flow and eddies) of irrigation/cooling fluid over its surface, which in turn provides more uniform cooling of the tip electrode, particularly where the tip electrode is elongated. In one embodiment, the tip electrode has a longitudinal axis, an outer ring surface generally perpendicular to the longitudinal axis, and an outer cylindrical surface extending distally from the outer ring surface along the longitudinal axis. Openings are provided in the outer ring surface to permit fluid (e.g., saline) to pass from an interior of the tip electrode to the outer ring surface and flow in a laminar manner over the cylindrical surface.

In another embodiment, a catheter in accordance with the present invention includes a catheter body having an outer wall, proximal and distal ends, and at least one lumen extending therethrough. A tip section distal the catheter body includes an irrigated tip electrode and a segment of flexible tubing with at least one lumen therethrough. The tip electrode has a longitudinal axis, a first outer ring surface generally perpendicular to the longitudinal axis, a first outer cylindrical surface extending distally from the first outer ring surface along the longitudinal axis, a second outer ring surface located at a distal end of the first outer cylindrical surface and generally perpendicular to the longitudinal axis, and a second outer cylindrical surface extending distally from the second outer ring surface. Openings are provided in the ring surfaces to permit fluid to pass from an interior of the tip electrode to the outer ring surfaces and flow in a laminar manner over the respective outer cylindrical surface extending therefrom.

In more detailed embodiments, each of the surfaces from which another surface extends distally has a greater diameter than the surface extending therefrom and/or each of the surfaces from which another surface extends is concentric with the surface extending therefrom. In other more detailed embodiment, the openings are angled so as to direct fluid passing therethrough to flow in a direction generally parallel with the outer cylindrical surfaces Moreover, the tip electrode may be formed from a shell and a plug, the shell being formed from a solid cylindrical bar that is milled on its outer surface to provide the stepped profile and drilled in its interior to form a chamber that feeds fluid to the outer surface of the tip electrode.

BRIEF DESCRIPTION OF THE DRAWINGS

These and other features and advantages of the present invention will be better understood by reference to the following detailed description when considered in conjunction with the accompanying drawings wherein like reference numbers represent corresponding parts throughout:

FIG. 2 is a side cross-sectional view of a catheter body according to the invention, including the junction between a catheter body and a tip section;

FIG. 3 is an isometric view of an embodiment of a tip electrode with a stepped profile;

FIG. 4 is an isometric view of an alternative embodiment of a tip electrode with a two-stepped profile;

DETAILED DESCRIPTION OF THE INVENTION

In the following description of the preferred embodiments, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

Figure 1:
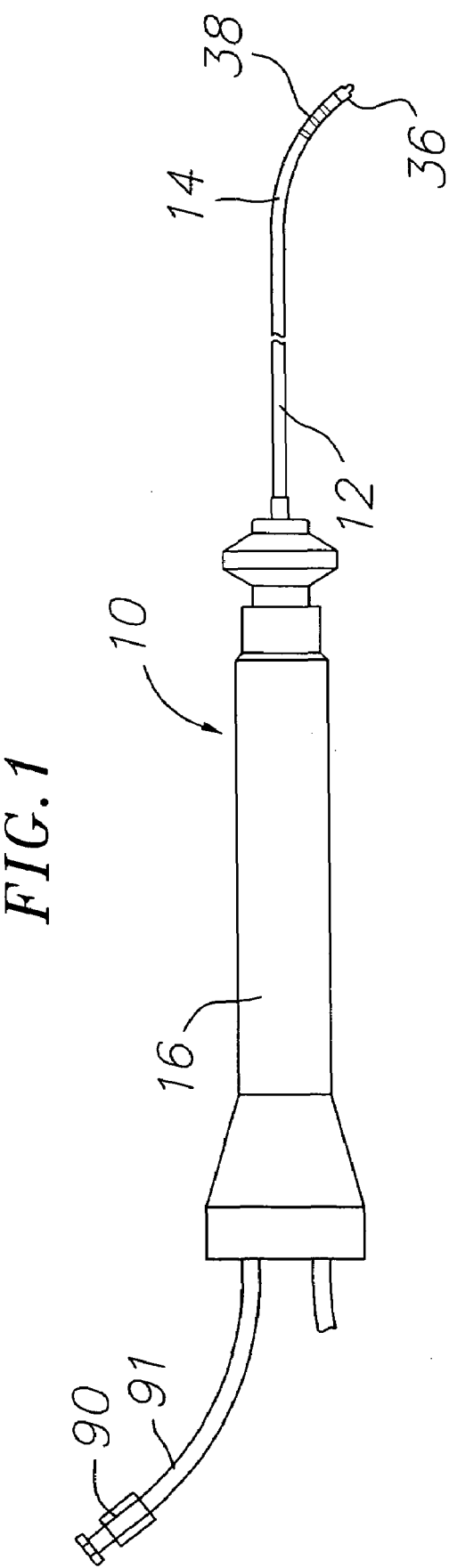
FIG. 1 is a side view of an embodiment of the catheter of the invention.

In an embodiment of the invention, there is provided a deflectable catheter with an irrigated tip having a stepped profile which provides a laminar flow of fluid over the tip surface for more uniform cooling of the tip surface. As shown in FIG. 1, catheter 10 comprises an elongated catheter body 12 having proximal and distal ends, a tip section 14 at the distal end of the catheter body 12, and a control handle 16 at the proximal end of the catheter body 12.

With reference to FIGS. 1-2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the central lumen 18 of the catheter body 12 are lead wires, an irrigation/infusion tube, and a compression coil 44 through which a puller wire 42 extends. A single lumen catheter body may be preferred over a multi-lumen body because it has been found that the single lumen body permits better tip control when rotating the catheter. The single lumen permits the lead wires, infusion tube, and the puller wire surrounded by the compression coil to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate an infusion tube, a puller wire, lead wires, and any other wires, cables or tubes. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

In one embodiment, the catheter has an outer wall 22 with an outer diameter from about 0.090 inch to about 0.94 inch and an inner diameter of from about 0.061 inch to about 0.065 inch and the polyimide stiffening tube 20 has an outer diameter of from about 0.060 inch to about 0.064 inch and an inner diameter of from about 0.051 inch to about 0.056 inch.

Figure 3A:
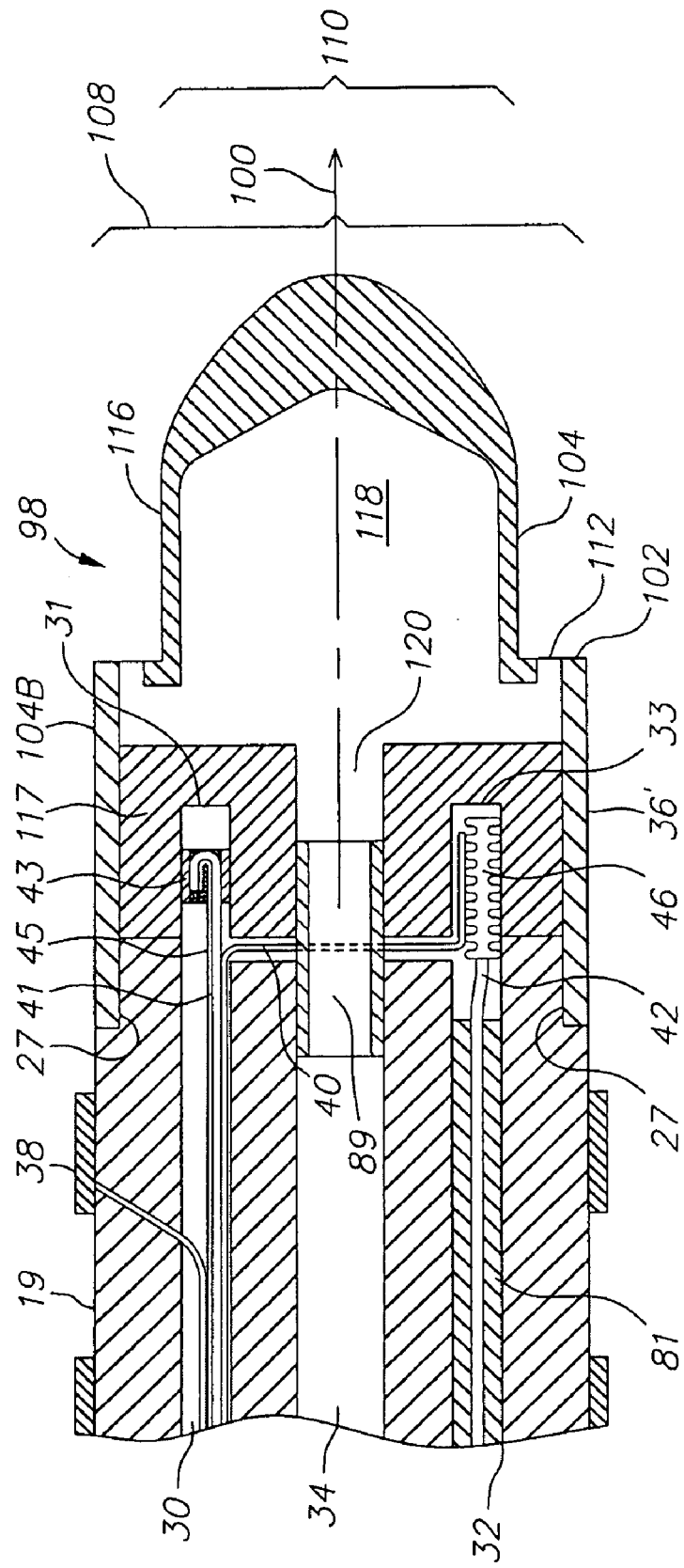
FIG. 3A is a side cross-sectional view of the tip electrode of FIG. 3.
Figure 3B:
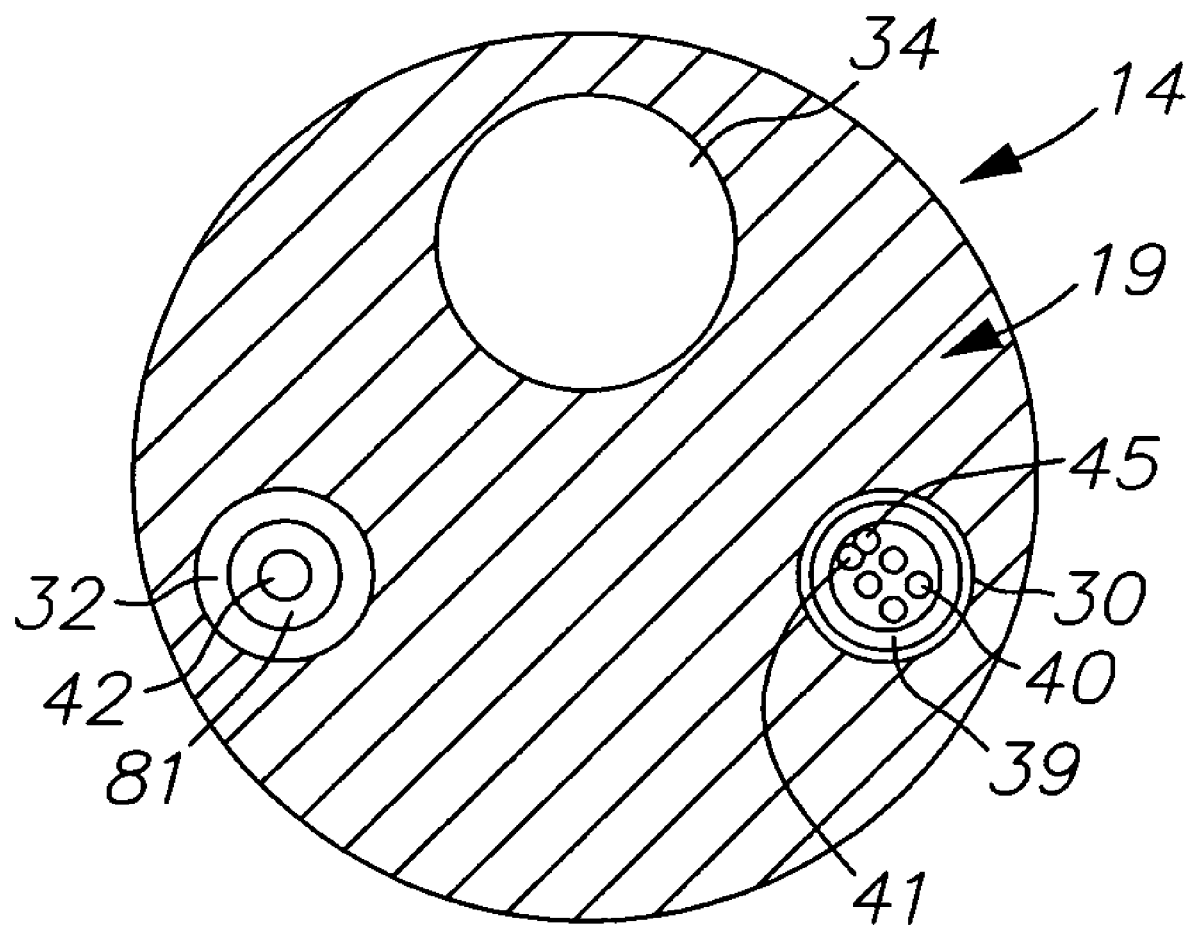
FIG. 3B is a longitudinal cross-sectional view of the tip section of FIG. 2, taken along line 3B-3B.

As shown in FIGS. 3, 3A and 3B, the tip section 14 comprises a tip electrode 36 and a short section of tubing 19. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 french, more preferably 7 french. The size of the lumens is not critical. In one embodiment, the tip section 14 has an outer diameter of about 7 french (0.092 inch) and multiple lumens. In the illustrated embodiment, a first lumen 30 and a second lumen 32 are generally about the same size, each having a diameter of from about 0.020 inch to about 0.024 inch, preferably 0.022 inch, with a third lumen 34 having a slightly larger diameter of from about 0.032 inch to about 0.038 inch, preferably 0.036 inch.

A means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and tip section, which allows this junction to bend smoothly without folding or kinking.

Referring to FIGS. 3 and 3A, the tip electrode 36 has a stepped profile with step 98 between its proximal and distal ends in accordance with the present invention. The stepped profile enables a laminar flow (or at least minimizes turbulent flow and/or eddies) of irrigation/cooling fluid over outer surface of the tip electrode, which in turn provides more uniform cooling of the tip electrode. In the illustrated embodiment of FIGS. 3 and 3A, the tip electrode 36' has a longitudinal axis 100, an outer ring surface 102 generally perpendicular to the longitudinal axis 100, and an outer cylindrical surface 104 extending distally from the ring surface 102 along the longitudinal axis 100. The ring surface 102 has a diameter 108 which is greater than a diameter 110 of the cylindrical surface 104, and the two surfaces 102 and 104 are concentric about the longitudinal axis 100.

A plurality of openings 112 are formed in the ring surface 102 spanning its circumference to permit fluid to pass from an interior chamber 118 of the tip electrode 36' to the outer ring surface 102 and flow continuously in a laminar manner over the cylindrical surface 104. By providing openings 112 that are angled to direct the flow of fluid in a direction generally parallel to the outer surface the tip electrode, there can be more uniform cooling of the outer surface. Accordingly, the fluid can flow in a sheet-like manner over the cylindrical surface 104 with a generally uniform thickness and direction of flow such that the cylindrical surface 104 can be covered with a blanket or layer of fluid with little, if any, turbulence. Such laminar flow advantageously facilitates more uniform cooling of the cylindrical surface 104.

In the illustrated embodiment of FIG. 3, there are eight openings, generally equi-sized, equi-shaped and equi-angular about the longitudinal axis 100. It is understood by one of ordinary skill in the art that the position, size, and arrangement of the openings can be varied as desired. The plurality of openings may range between about two and twelve, preferably between about four and ten, and more preferably about eight.

Figure 4A:
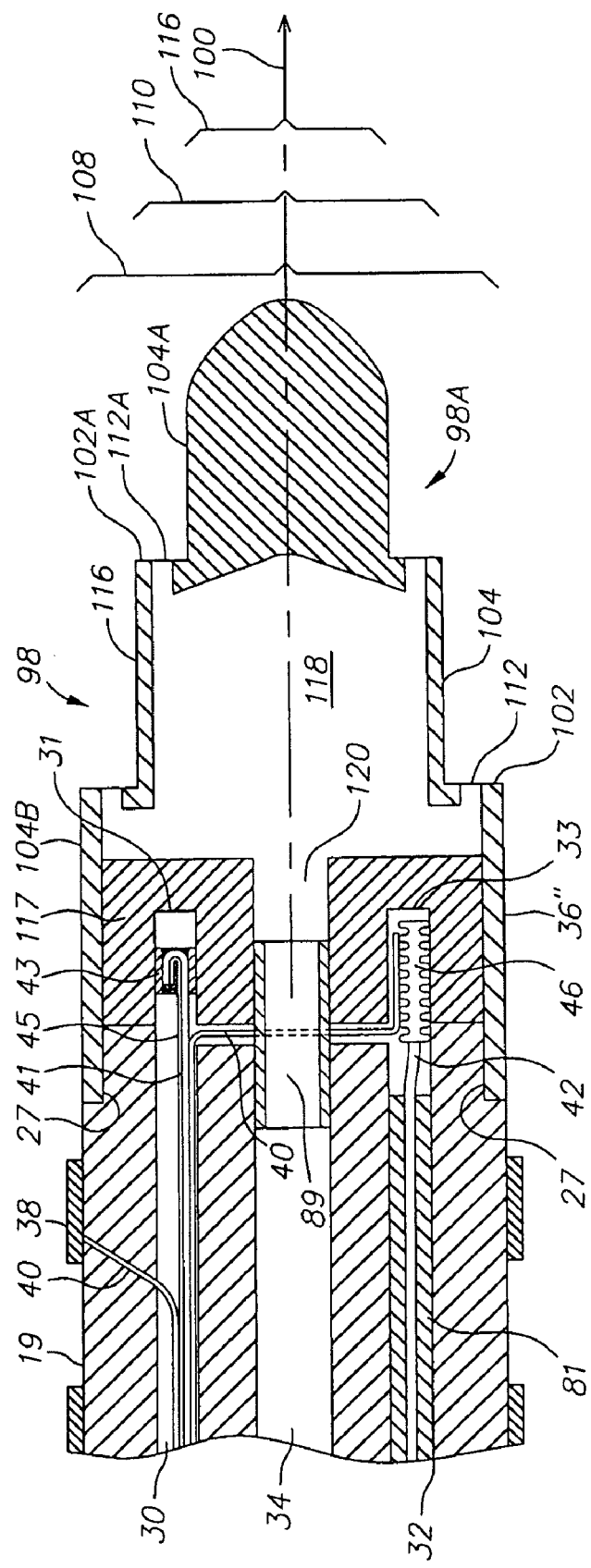
FIG. 4A is a side cross-sectional view of the tip electrode of FIG. 4.

In an alternative embodiment, as illustrated in FIGS. 4 and 4A, a tip electrode 36" has a two-stepped profile (steps 98 and 98A) by also providing a second outer ring surface 102A located at a distal end of the first outer cylindrical surface 104, and a second outer cylindrical surface 104A that extends distally from the second outer ring surface 102A. In the illustrated embodiment, the surfaces 102, 102A, 104 and 104A are all concentric with each other about the longitudinal axis 100. A diameter of the second outer ring 102A is generally equal to the diameter 110 of the first cylindrical surface 104, and a diameter 116 of the second outer cylindrical surface 104A is smaller than the diameters 110 and 108.

Accordingly, each laminar-flow-enabling step 98, 98A of the tip electrode is formed from a serial combination of an outer ring surface having a larger diameter and a distal outer circumferential surface with a smaller diameter. And, where there are more than one laminar-flow-enabling step, an outer cylindrical surface connects two outer ring surfaces and/or an outer ring surface connects two outer cylindrical surfaces. Regardless of the variation, the most distal outer cylindrical surface tapers or is otherwise configured at its distal end to form an atraumatic distal end of the tip electrode 36.

A plurality of openings 112A are formed in the second outer ring surface 102A spanning its circumference to permit fluid to pass from the interior chamber 118 to the outer ring surface 102A and flow continuously in a laminar manner over the cylindrical surface 104A, as described above. The tip section 36" of the illustrated embodiment of FIG. 4A has eight openings 112A that are in radial alignment with the openings 112, although it is understood by one of ordinary skill in the art that the openings 112 and 112A need not be the same in terms of plurality, size, shape and/or arrangement.

A suitable embodiment of the tip electrode 36' and 36" has a shell 116 and a plug 117 which jointly define the chamber 118 that is fed by the third lumen 34 as bridged to the tip electrode by a second infusion tube segment 89 extending from the lumen 34 to a fluid passage 120 formed in the plug 117. The chamber 118 as formed by the shell and plug avoids, or at least minimizes the use of fluid passages within the tip electrode, which in turn facilitates the flow of fluid in a laminar manner as described above.

In the illustrated embodiments, the outer surface of the shell 116 includes the aforementioned ring surface(s) and the cylindrical surfaces, and further includes a third cylindrical surface 104B that is proximal of the first outer ring surface 102. The diameter of the third cylindrical surface 104B is generally equal to the diameter 108 and the diameter of the tubing 19. To that end, a means for attaching the tip electrode 36 to the tubing 19 is illustrated in FIGS. 3A and 4A. The shell 116 extends proximally past a proximal end of the plug 117 to form an inner circumferential surface which is received by an outer circumferential notch 27. The tubing and the shell 116 are attached by glue or the like.

The interior chamber 118 of the tip electrode is sealed and partially filled by the plug 117. A suitable method of manufacture using a shell and a plug is described in U.S. patent application Ser. No. 11/058,434, the entire disclosure of which is incorporated herein by reference. In the present invention, the tip electrode, including the shell and the plug may be made of any suitable material, for example, platinum-iridium bar (90% platinum/10% iridium). The shell may be formed from a solid cylindrical rod or bar that is milled on its outer surface to form the stepped profile and drilled in the interior to form the chamber 118. The openings 112 and 112A are drilled in the outer ring surfaces 102 and 102A of the shell, and the chamber 118 is cleaned of drilling debris preferably before the plug 117 is inserted into the shell 116.

The tip electrode 36 is connected to a separate lead wire 40. The lead wire 40 extends through the first lumen 30 of tip section 14 (FIG. 3c), the central lumen 18 of the catheter body 12 (FIG. 2), and the control handle 16 (FIG. 6), and terminate at their proximal end in an input jack (not shown) that may be plugged into an appropriate monitor (not shown). The portion of the lead wire 40 extending through the central lumen 18 of the catheter body 12, control handle 16 and proximal end of the tip section 14 may be enclosed within a protective sheath 39, which can be made of any suitable material, preferably polyimide. The protective sheath 39 is anchored at its distal end to the proximal end of the tip section 14 by gluing it in the first lumen 30 with polyurethane glue or the like. The lead wire 40 is attached to the tip electrode 36 by any conventional technique. Connection of a lead wire 40 to the tip electrode 36 is accomplished, for example, by welding the lead wire 40 into a first hole 33 in the plug 112.

One or more ring electrodes 38 can be positioned over the flexible tubing 19 of the tip section 14. The presence and number of ring electrodes 38 can vary as desired. Connection of a lead wire 40 to a ring electrode 38 is preferably accomplished by first making a small hole through the tubing 19. Such a hole can be created, for example, by inserting a needle through the tubing 19 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A temperature sensing means may be provided for the tip electrode 36. Any conventional temperature sensing means, e.g., a thermocouple or thermistor, may be used. With reference to FIGS. 3 and 4, a preferred temperature sensing means for the tip electrode 36 comprises a thermocouple formed by a wire pair. One wire of the wire pair is a copper wire 41, e.g., a number "40" copper wire. The other wire of the wire pair is a constant an wire 45, which gives support and strength to the wire pair. The wires 41 and 45 of the wire pair are electrically isolated from each other except at their distal ends where they contact and are twisted together, covered with a short piece of plastic tubing 43, e.g., polyimide, and covered with epoxy. The plastic tubing 43 is then attached in a second blind hole 31 formed in the plug 117 of the tip electrode 36, by polyurethane glue or the like. The wires 41 and 45 extend through the first lumen 30 in the tip section 14. Within the catheter body 12 the wires 41 and 45 extend through the protective sheath 39 with the lead wires 40. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143E/37C sold by Thermometrics (New Jersey).

The puller wire 42 extends through the catheter body 12 which is anchored at its proximal end to the control handle 16 and anchored at its distal end to the tip section 14. The puller wire 42 is made of any suitable metal, such as stainless steel or Nitinol, and is preferably coated with TEFLON® (polytetrafluoroethylene) or the like. The coating imparts lubricity to the puller wire 42. The puller wire 42 preferably has a diameter ranging from about 0.006 to about 0.010 inches.

As shown in FIG. 2, a compression coil 44 is situated within the catheter body 12 in surrounding relation to the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. The Teflon® coating on the puller wire 42 allows it to slide freely within the compression coil 44. If desired, particularly if the lead wires 40 are not enclosed by a protective sheath 39, the outer surface of the compression coil 44 can be covered by a flexible, non-conductive sheath, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

With reference to FIGS. 3, 3B and 4, the puller wire 42 extends into the second lumen 32 of the tip section 14. The puller wire 42 is anchored at its distal end to the tip electrode 36 within a second blind hole 33 formed in the plug 117. A preferred method for anchoring the puller wire 42 within the tip electrode 36 is by crimping metal tubing 46 to the distal end of the puller wire 42 and soldering the metal tubing 46 inside the blind hole 33. Anchoring the puller wire 42 within the tip electrode 36 provides additional support, reducing the likelihood that the tip electrode 36 will fall off the tubing 19. Alternatively, the puller wire 42 can be attached to the side of the tip section 14. Within the second lumen 32 of the tip section 14, the puller wire 42 extends through a plastic, preferably TEFLON® (polytetrafluoroethylene), sheath 81, which prevents the puller wire 42 from cutting into the wall of the tip section 14 when the tip section is deflected.

An infusion tube is provided within the catheter body 12 for infusing fluids, e.g., saline, to cool the tip electrode 36. The infusion tube may also be used to infuse drugs or to collect tissue or fluid samples. The infusion tube may be made of any suitable material, and is preferably made of polyimide tubing. A preferred infusion tube has an outer diameter of from about 0.32 inch to about 0.036 inch and an inner diameter of from about 0.28 inch to about 0.032 inch.

With reference to FIGS. 1, 2 and 3, a first infusion tube segment 88 extends through the central lumen 18 of the catheter body 12 and terminates in the proximal end of the third lumen 34 of the tip section 14. The distal end of the first infusion tube segment 88 is anchored in the third lumen 34 by polyurethane glue or the like. The proximal end of the first infusion tube segment 88 extends through the control handle 16 and terminates in a luer hub 90 or the like at a location proximal to the control handle.

With reference to FIGS. 3 and 4, the second infusion tube segment 89 is provided at the distal end of the third lumen 34 and extends into the fluid passage 120 of the tip electrode 36. The second infusion tube segment 89 is anchored within the third lumen 34 and the fluid passage 120 by polyurethane glue or the like. The second infusion tube segment 89, like the puller wire 42, provides additional support for the tip electrode. In practice, fluid may be injected into the first infusion tube segment 88 through the luer hub 90, and flows through the first infusion tube segment 88, through the third lumen 34, through the second infusion tube segment 89 into the fluid passage 120 in the tip electrode 36, and out the irrigation openings 112, 112A of tip electrode 36. In accordance with the present invention, the irrigation openings 112/112A provide for effective irrigation of the surface of the tip electrode 36 by directing the exiting irrigation fluid over the tip electrode 36 in a manner that increases surface contact between the irrigation fluid and the surface of the tip electrode 36. The strength of the RF current no longer needs to be limited by the interface temperature when the tip electrode 36 is irrigated, therefore allowing the current to be increased. This results in lesions which tend to be larger and more spherical.

Figure 5:
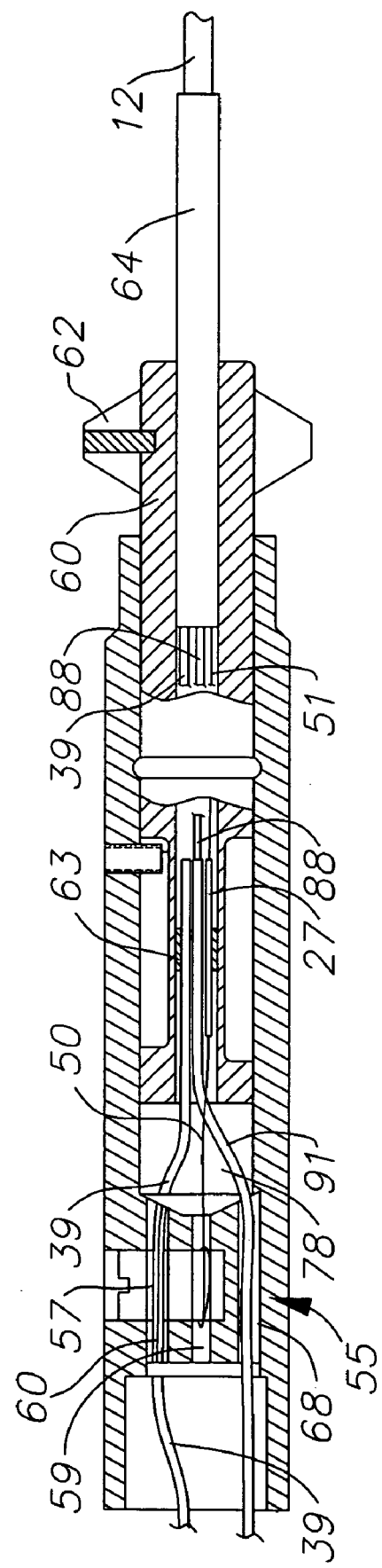
FIG. 5 is a side cross-sectional view of an embodiment of a control handle.

Referring to FIG. 5, longitudinal movement of the puller wire 42 relative to the catheter body 12, which results in deflection of the tip section 14, is accomplished by suitable manipulation of the control handle 16. As shown in FIG. 5, the distal end of the control handle 16 comprises a piston 54 with a thumb control 56 for manipulating the puller wire 42. The proximal end of the catheter body 12 is connected to the piston 54 by means of a shrink sleeve 28.

The puller wire 42, lead wires 40, thermocouple wires 41 and 45, and first infusion tube segment 88 extend through the piston 54. The puller wire 42 is anchored to an anchor pin 57, located proximal to the piston 54. Within the control handle 16, the lead wires 40 and thermocouple wires 41 and 45 are within the protective sheath 39. Within the piston 54, the first infusion tube segment 88 extends into another protective sheath 91, preferably made of polyurethane, similar to the side arm 94, described above. The protective sheathes 39 and 91 are anchored to the piston 54, preferably by polyurethane glue or the like at a glue joint 53, allowing the first infusion tube segment 88, lead wires 40 and thermocouple wires 41 and 45 longitudinal movement within the control handle 16 so that they does not break when the piston 54 is adjusted to manipulate the puller wire 42. Within the piston 54, the puller wire 42 extends through a transfer tube 27, preferably a polyimide tube, to allow longitudinal movement of the puller wire near the glue joint 53.

The piston 54 lies within the barrel 55 of the control handle. The barrel 55 is generally solid having a piston chamber for receiving the piston 54. Extending proximally from the piston chamber are three longitudinal holes 58, 59 and 60 and a transverse hole for receiving the anchor pin 57. The second longitudinal hole 59 is in communication with the transverse hole. The first infusion tube segment 88 within the protective sheath 91 extends through the first longitudinal hole 40. The puller wire 42 extends through the second longitudinal hole 59 and is anchored to the anchor pin 57 in the transverse hole. The thermocouple wires 41 and 45 and lead wires 40 within the protective sheath 39 extend through the third longitudinal hole 60. Between the distal end of the longitudinal holes 58, 59 and 60 and the proximal end of the piston 54, chamber 62 provides additional space to avoid undesirable bending of the first infusion tube segment 88. Preferably the space has a length of at least 0.50 inch and more preferably about from about 0.60 inch to about 0.90 inch.

The catheter can be adapted to carry an electromagnetic sensor near the tip electrode 36. An electromagnetic sensor cable can extend through the first lumen 30 of the tubing 19, or a fourth lumen if provided, through the central lumen 18 of the catheter body 12, and into the control handle 16. The electromagnetic sensor cable can extend out the proximal end of the control handle 16 within an umbilical cord to a sensor control module that houses a circuit board. Alternatively, the circuit board can be housed within the control handle 16. The electromagnetic sensor cable can comprise multiple wires encased within a plastic covered sheath. In the sensor control module, the wires of the electromagnetic sensor cable are connected to the circuit board. The circuit board amplifies the signal received from the electromagnetic sensor and transmits it to a computer in a form understandable by the computer by means of the sensor connector at the proximal end of the sensor control module. Also, because the catheter is designed for single use only, the circuit board preferably contains an EPROM chip which shuts down the circuit board approximately 24 hours after the catheter has been used. This prevents the catheter, or at least the electromagnetic sensor, from being used twice. A preferred electromagnetic mapping sensor has a length of from about 6 mm to about 7 mm and a diameter of about 1.3 mm.

The foregoing description of the preferred embodiments of the present invention have been presented for the purpose of illustration and description. It is not intended to be exhaustive or to limit the invention to the precise form disclosed. Workers skilled in the art and technology to which this invention pertains will appreciate that alterations and changes in the described structure may be practiced without meaningfully departing from the principal, spirit and scope of this invention. It is intended that the scope of this application not be limited by this detailed description, but by the claims and the equivalents to the claims appended hereto.

What is claimed is:

1. An irrigated ablation catheter, comprising:
   a catheter body; and
   a tip section distal the catheter body having an irrigated tip electrode, wherein the irrigated tip electrode comprises:
      a longitudinal axis,
      a first outer ring surface generally perpendicular to the longitudinal axis,
      a first outer cylindrical surface extending distally from the first outer ring surface along the longitudinal axis,
      a second outer ring surface at a distal end of the first outer cylindrical surface and generally perpendicular to the longitudinal axis,
      a second outer cylindrical surface extending distally from the second outer ring surface; and
      openings provided in the ring surfaces to pass fluid from interior of the tip electrode to flow in a laminar manner over the outer cylindrical surfaces.

2. An irrigated catheter for ablating tissue, comprising:
   a catheter body having an outer wall, proximal and distal ends, and at least one lumen extending therethrough;
   a tip section comprising a segment of flexible tubing having proximal and distal ends and at least one lumen therethrough, the proximal end of the tip section being fixedly attached to the distal end of the catheter body;
   a tip electrode having a proximal and distal end and a longitudinal axis, wherein the proximal end of the tip electrode is fixedly attached to the distal end of the tip section, the tip electrode comprising:
      a proximal outer ring surface and a distal outer ring surface, the proximal outer ring surface having a diameter greater than a diameter of the distal outer ring surface, the proximal and distal ring surfaces being generally perpendicular to the longitudinal axis;
      a first outer cylindrical surface connecting the proximal and distal outer ring surfaces;
      a second outer cylindrical surface extending distally from the distal outer ring surface, the second outer cylindrical surface having a diameter lesser than the diameter of the first outer cylindrical surface; and
   openings formed in the outer ring surfaces to pass fluid from interior of the tip electrode to flow in a laminar manner over the outer cylindrical surfaces.

3. An irrigated ablation catheter of claim 2, wherein a distal end of the second outer cylindrical surface tapers to form an atraumatic distal end of the tip electrode.

4. An irrigated catheter of claim 2, further including a control handle at the proximal end of the catheter body.

5. An irrigated catheter of claim 2, further including means for deflecting the tip section.

6. An irrigated catheter of claim 5, wherein the deflecting means comprises a puller wire having a proximal end and a distal end, the puller wire extending from a control handle, through the catheter body and into a lumen in the tip section, whereby manipulation of the control handle moves the puller wire resulting in deflection of the tip section.

7. An irrigated catheter of claim 2, wherein the tip electrode comprises a shell and a plug.

8. The irrigated catheter of claim 2, further including a temperature sensing means mounted in the tip electrode wherein the temperature sensing means comprises a thermocouple.

9. The irrigated catheter of claim 2, further including an electromagnetic mapping sensor mounted at or near the tip electrode for producing electrical signals indicative of a location of the electromagnetic mapping sensor.

\* \* \* \* \*